US007813784B2

(12) United States Patent
Marquart et al.

(10) Patent No.: US 7,813,784 B2
(45) Date of Patent: Oct. 12, 2010

(54) INTERACTIVE COMPUTER-ASSISTED SURGERY SYSTEM AND METHOD

(75) Inventors: Joel Marquart, Davie, FL (US); Randall Hand, Pembroke Pines, FL (US); Arthur E. Quaid, III, Hollywood, FL (US); Louis K. Arata, Mentor, OH (US); Rony A. Abovitz, Hollywood, FL (US); Marwan Sati, Mississauga (CA)

(73) Assignees: MAKO Surgical Corp., Fort Lauderdale, FL (US); Biomet Manufacturing Corp., Warsaw, IN (US)

( * ) Notice: Subject to any disclaimer, the term of this patent is extended or adjusted under 35 U.S.C. 154(b) by 1182 days.

(21) Appl. No.: 11/199,559

(22) Filed: Aug. 8, 2005

(65) Prior Publication Data
US 2006/0058616 A1 Mar. 16, 2006

Related U.S. Application Data

(63) Continuation of application No. 11/006,481, filed on Dec. 6, 2004, now abandoned, which is a continuation of application No. 10/772,083, filed on Feb. 4, 2004, now abandoned.

(60) Provisional application No. 60/444,824, filed on Feb. 4, 2003.

(51) Int. Cl.
*A61B 5/05* (2006.01)
(52) U.S. Cl. ............ 600/424; 600/426; 600/429; 606/130
(58) Field of Classification Search ............. 600/424, 600/471; 434/267; 606/130
See application file for complete search history.

(56) References Cited

U.S. PATENT DOCUMENTS

| 4,979,949 A | * | 12/1990 | Matsen et al. ............ 606/53 |
|---|---|---|---|
| 5,389,101 A | | 2/1995 | Heilbrun et al. |
| 5,638,819 A | | 6/1997 | Manwaring et al. |
| 5,682,886 A | | 11/1997 | Delp et al. |
| 5,751,548 A | | 5/1998 | Hall et al. |
| 5,879,297 A | | 3/1999 | Haynor et al. |
| 5,980,535 A | | 11/1999 | Barnett et al. |
| 6,005,548 A | | 12/1999 | Latypov et al. |
| 6,166,746 A | | 12/2000 | Inada et al. |
| 6,167,292 A | | 12/2000 | Badano et al. |
| 6,285,902 B1 | | 9/2001 | Kienzle, III et al. |
| 6,423,002 B1 | * | 7/2002 | Hossack ............ 600/439 |
| 6,478,802 B2 | | 11/2002 | Kienzle, III et al. |
| 6,643,535 B2 | | 11/2003 | Damasco et al. |

(Continued)

OTHER PUBLICATIONS

Luck, J.P., "Development and Analysis of a Real-Time Human Motion Tracking System," Colorado School of Mines, Engineering Division Whoff Publications, 2002 Sections 3.1-3.2.3.

(Continued)

*Primary Examiner*—Long V Le
*Assistant Examiner*—Ellsworth Weatherby
(74) *Attorney, Agent, or Firm*—Fay Sharpe LLP

(57) ABSTRACT

A system and method for providing computer assistance for performing a medical procedure provides a graphical user interface to guide and/or assist a user, for example a surgeon, performing the medical procedure, whether surgical or non-surgical. The computer-assisted system comprises a software application that may be used for a medical procedure.

11 Claims, 10 Drawing Sheets

U.S. PATENT DOCUMENTS

| | | | |
|---|---|---|---|
| 7,048,745 B2 * | 5/2006 | Tierney et al. | 606/130 |
| 2002/0082492 A1 | 6/2002 | Grzeszczuk | |
| 2002/0193686 A1 * | 12/2002 | Gilboa | 600/424 |
| 2003/0093103 A1 * | 5/2003 | Malackowski et al. | 606/170 |
| 2004/0044295 A1 * | 3/2004 | Reinert et al. | 600/587 |
| 2004/0152970 A1 | 8/2004 | Hunter et al. | |
| 2004/0152972 A1 * | 8/2004 | Hunter | 600/424 |
| 2004/0254771 A1 | 12/2004 | Riener et al. | |

OTHER PUBLICATIONS

DiFranci, D.E., et al. Recovery of 3D Articulated Motion from 2D Correspondences, Cambridge Research Laboratory Technical Report CRL 99/7, Dec. 1999, Sections 4.0-4.4, Fig. 6.

International Search Report dated Oct. 28, 2005.

* cited by examiner

INTERACTIVE COMPUTER-ASSISTED SURGERY SYSTEM AND METHOD

This patent application is a continuation of U.S. patent application Ser. No. 11/006,481, entitled "Interactive Computer-Assisted Surgery System and Method," filed Dec. 6, 2004, now abandoned which is a continuation of U.S. patent application Ser. No. 10/772,083, entitled "Interactive Computer-Assisted Surgery System and Method," filed Feb. 4, 2004; now abandoned and claims the benefit of U.S. provisional patent application Ser. No. 60/444,824, entitled "Interactive Computer-Assisted Surgery System and Method", filed Feb. 4, 2003, the disclosure of which is incorporated herein by reference. This application relates to the following U.S. provisional patent applications: Ser. No. 60/444,975, entitled "System and Method for Providing Computer Assistance With Spinal Fixation Procedures"; Ser. No. 60/445,078, entitled "Computer-Assisted Knee Replacement Apparatus and Method"; Ser. No. 60/444,989, entitled "Computer-Assisted External Fixation Apparatus and Method"; Ser. No. 60/444,988, entitled "Computer-Assisted Knee Replacement Apparatus and Method"; Ser. No. 60/445,002, entitled "Method and Apparatus for Computer Assistance With Total Hip Replacement Procedure"; Ser. No. 60/445,001, entitled "Method and Apparatus for Computer Assistance With Intramedullary Nail Procedure"; and Ser. No. 60/319,924, entitled "Portable, Low-Profile Integrated Computer, Screen and Keyboard for Computer Surgery Applications"; each of which was filed on Feb. 4, 2003 and is incorporated herein by reference. This application also relates to the following applications: U.S. patent application Ser. No. 10/771,850, entitled "System and Method for Providing Computer Assistance With Spinal Fixation Procedures"; U.S. patent application Ser. No. 10/772,139, entitled "Computer-Assisted Knee Replacement Apparatus and Method"; U.S. patent application Ser. No. 10/772,142, entitled Computer-Assisted External Fixation Apparatus and Method"; U.S. patent application Ser. No. 10/772,085, entitled "Computer-Assisted Knee Replacement Apparatus and Method"; U.S. patent application Ser. No. 10/772,092, entitled "Method and Apparatus for Computer Assistance With Total Hip Replacement Procedure"; U.S. patent application Ser. No. 10/771,851, entitled "Method and Apparatus for Computer Assistance With Intramedullary Nail Procedure"; and U.S. patent application Ser. No. 10/772,137, entitled "Portable Low-Profile Integrated Computer, Screen and Keyboard for Computer Surgery Applications"; each of which was filed on Feb. 4, 2004 and is incorporated herein by reference.

TECHNICAL FIELD OF THE INVENTION

The present invention relates generally to computer-assisted surgery systems and surgical navigation systems.

BACKGROUND OF THE INVENTION

Image-based surgical navigation systems display the positions of surgical tools with respect to preoperative (prior to surgery) or intraoperative (during surgery) image data sets. Two and three dimensional image data sets are used, as well as time-variant images data (i.e. multiple data sets taken at different times). Types of data sets that are primarily used include two-dimensional fluoroscopic images and three-dimensional data sets include magnetic resonance imaging (MRI) scans, computer tomography (CT) scans, positron emission tomography (PET) scans, and angiographic data. Intraoperative images are typically fluoroscopic, as a C-arm fluoroscope is relatively easily positioned with respect to patient and does not require that a patient be moved. Other types of imaging modalities require extensive patient movement and thus are typically used only for preoperative and post-operative imaging.

The most popular navigation systems make use of a tracking or localizing system to track tools, instruments and patients during surgery. These systems locate in predefined coordinate space specially recognizable markers that are attached or affixed to, or possibly inherently a part of, an object such as an instrument or a patient. Markers can take several forms, including those that can be located using optical (or visual), electromagnetic, radio or acoustic methods. Furthermore, at least in the case of optical or visual systems, location of an object's position may be based on intrinsic features or landmarks that, in effect, function as recognizable markers. Markers will have a known, geometrical arrangement with respect to, typically, an end point and/or axis of the instrument. Thus, objects can be recognized at least in part from the geometry of the markers (assuming that the geometry is unique), and the orientation of the axis and location of endpoint within a frame of reference deduced from the positions of the markers.

Present day tracking systems are typically optical, functioning primarily in the infrared range. They usually include a stationary stereo camera pair that is focused around the area of interest and sensitive to infrared radiation. Markers emit infrared radiation, either actively or passively. An example of an active marker is a light emitting diodes (LEDs). An example of a passive marker is a reflective marker, such as ball-shaped marker with a surface that reflects incident infrared radiation. Passive systems require a an infrared radiation source to illuminate the area of focus. A magnetic system may have a stationary field generator that emits a magnetic field that is sensed by small coils integrated into the tracked tools.

Most CAS systems are capable of continuously tracking, in effect, the position of tools (sometimes also called instruments). With knowledge of the position of the relationship between the tool and the patient and the patient and an image data sets, a system is able to continually superimpose a representation of the tool on the image in the same relationship to the anatomy in the image as the relationship of the actual tool to the patient's anatomy. To obtain these relationships, the coordinate system of the image data set must be registered to the relevant anatomy of the actual patient portions of the of the patient's anatomy in the coordinate system of the tracking system. There are several known registration methods.

In CAS systems that are capable of using two-dimensional image data sets, multiple images are usually taken from different angles and registered to each other so that a representation of the tool or other object (which can be real or virtual) can be, in effect, projected into each image. As the position of the object changes in three dimensional space, its projection into each image is simultaneously updated. In order to register two or more two-dimensional data images together, the images are acquired with what is called a registration phantom in the field of view of the image device. In the case of a two dimensional fluoroscopic images, the phantom is a radio-translucent body holding radio-opaque fiducials having a known geometric relationship. Knowing the actual position of the fiducials in three dimensional space when each of the images are taken permits determination of a relationship between the position of the fiducials and their respective shadows in each of the images. This relationship can then be used to create a transform for mapping between points in three-dimensional space and each of the images. By knowing the positions of the fiducials with respect to the tracking system's frame of reference, the relative positions of tracked tools with respect to the patient's anatomy can be accurately indicated in each of the images, presuming the patient does not move after the image is acquired, or that the relevant are portions of the patient's anatomy is are tracked. A more detailed explanation of registration of fluoroscopic images and coordination of representations of objects in patient space superimposed in the images is found in U.S. Pat. No. 6,198, 794 of Peshkin, et al., entitled "Apparatus and method for planning a stereotactic surgical procedure using coordinated fluoroscopy".

SUMMARY OF THE INVENTION

A system and method for providing computer assistance for performing a medical procedure provides a graphical user interface to guide and/or assist a user, for example a surgeon, performing the medical procedure, whether surgical or non-surgical. The computer-assisted system comprises a software application that may be used for a medical procedure.

The invention is generally directed to improved computer-implemented methods and apparatus for further reducing the invasiveness of surgical procedures, eliminating or reducing the need external fixtures in certain surgical procedures, and/or improving the precision and/or consistency of surgical procedures. The invention finds particular advantage in orthopedic procedures involving implantation of devices, though it may also be used in connection with other types of surgical procedures.

Other aspects and features of the invention will become apparent to those ordinarily skilled in the art upon review of the following description of specific embodiments of the invention in conjunction with the accompanying figures.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE DRAWINGS

The preferred embodiment of the present invention and its advantages are best understood by referring to FIGS. 1 through 6B of the drawings.

In the following description, like numbers refer to like elements. References to "surgeon" include any user of a computer-assisted surgical system, a surgeon being typically a primary user.

Figure 1:
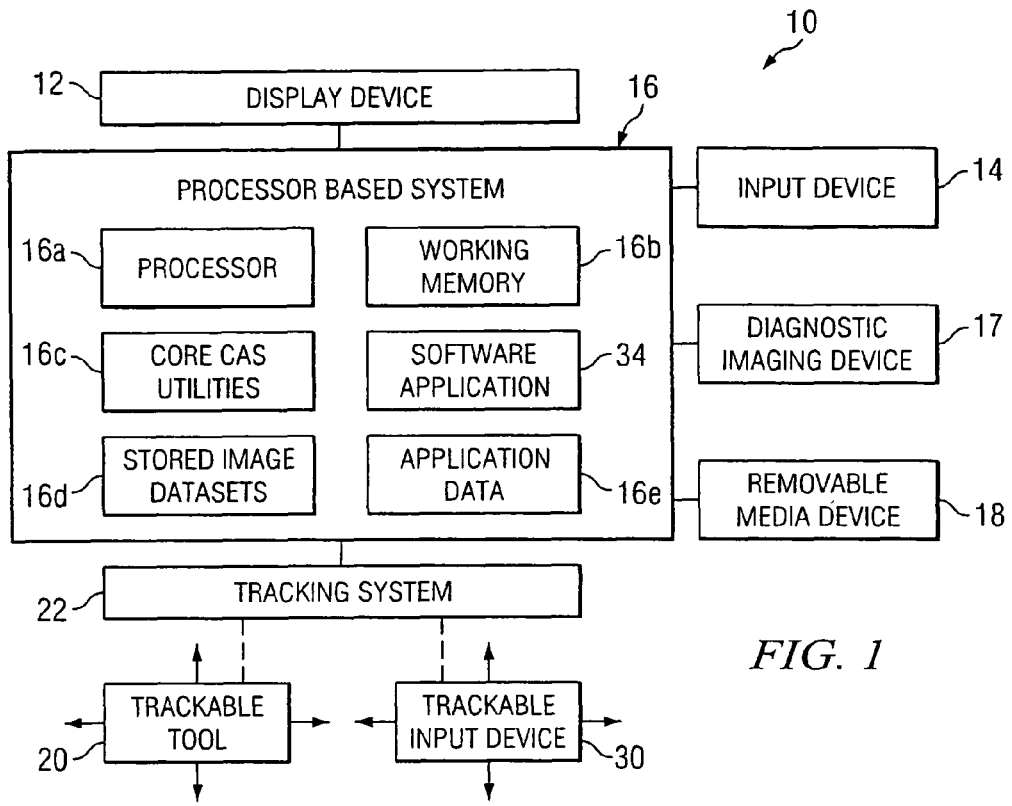
FIG. 1 is a block diagram of an exemplary interactive computer-assisted surgery system.

FIG. 1 is a block diagram of an exemplary computer-assisted surgery (CAS) system 10. Computer-assisted surgery system (CAS) 10 comprises a display device 12, an input device 14, and a processor-based system 16, for example a computer. Display device 12 may be any display device now known or later developed for displaying two-dimensional and/or three-dimensional diagnostic images, for example a monitor, a touch screen, a wearable display, a projection display, a head-mounted display, stereoscopic views, a holographic display, a display device capable of displaying image(s) projected from an image projecting device, for example a projector, and/or the like. Input device 14 may be any input device now known or later developed, for example, a keyboard, a mouse, a trackball, a trackable probe and/or the like. The processor-based system is preferably programmable and includes one or more processors 16a, working memory 16b for temporary program and data storage that will be used primarily by the processor, and storage for programs and data, preferably persistent, such as a disk drive. Removable media device 18 can also be used to store programs and/or transferred to or from the transfer programs.

Tracking system 22 continuously determines, or tracks, the position of one or more trackable markers disposed on, incorporated into, or inherently a part of surgical tools or instruments 20 with respect to a three-dimensional coordinate frame of reference. With information from the tracking system on the location of the trackable markers, CAS system 10 is programmed to be able to determine the three-dimensional coordinates of an endpoint or tip of a tool and, optionally, its primary axis using predefined or known (e.g. from calibration) geometrical relationships between trackable markers on the tool and the end point and/or axis of the tool. A patient, or portions of the patient's anatomy, can also be tracked by attachment of arrays of trackable markers.

The CAS system can be used for both planning surgical procedures (including planning during surgery) and for navigation. It is therefore preferably programmed with software for providing basic image guided surgery functions, including those necessary determining the position of the tip and axis of instruments and for registering a patient and preoperative and/or intraoperative diagnostic image data sets to the coordinate as core CAS utilities 16c. These capabilities allow the relationship of a tracked instrument to a patient to be displayed and constantly updated in real time by the CAS system overlaying a representation of the tracked instrument on or more graphical images of the patient's internal anatomy on display device 12. The graphical images are constructed from one or more stored image data sets 16d acquired from diagnostic imaging device 17. Imaging device may be a fluoroscope, such as a C-arm fluoroscope, capable of being positioned around a patient laying an operating table. It may also be a MR, CT or other type of imaging device in the room or permanently located elsewhere. Where more than one image is shown, as when multiple fluoroscopic images are simultaneously displayed of display device 12, the representation of the tracked instrument or tool is coordinated between the different images. However, CAS system can be used in some procedures without the diagnostic image data sets, with only the patient being registered. Thus, the CAS system need not support the use of diagnostic images in some applications—i.e. an imageless application.

Furthermore, as disclosed herein, the CAS system may be used to run application-specific programs or software 34 that are directed to assisting a surgeon with planning and/or navigation during specific types of procedures. For example, the software application 34 may display predefined pages or images corresponding to specific steps or stages of a surgical procedure. At a particular stage or part of a program, a surgeon may be automatically prompted to perform certain tasks or to define or enter specific data that will permit, for example, the program to determine and display appropriate placement and alignment of instrumentation or implants or provide feedback to the surgeon. Other pages may be set up to display diagnostic images for navigation and to provide certain data that is calculated by the system for feedback to the surgeon. Instead of or in addition to using visual means, the CAS system could also communicate information in ways, including using audibly (e.g. using voice synthesis) and tactilely, such as by using a haptic interface of device. For example, in addition to indicating visually a trajectory for a drill or saw on the screen, a CAS system may feedback to a surgeon information whether he is nearing some object or is on course with a audible sound or by application of a force or other tactile sensation to the surgeon's hand.

To further reduce the burden on the surgeon, the program may automatically detect the stage of the procedure by recognizing the instrument picked up by a surgeon and move immediately to the part of the program in which that tool is used. Application data 16e—data generated or used by the application—may also be stored processor-based system.

Various types of user input methods can be used to improve ease of use of the CAS system during surgery. One example uses speech recognition to permit a doctor to speak a command. Another example is the use of a tracked object to sense a gesture by a surgeon, which is interpreted as an input to the CAS system. The meaning of the gesture could further depend on the state of the CAS system or the current step in an application process executing on the CAS system. Again, as an example, a gesture may instruct the CAS system to capture the current position of the object. One way of detecting a gesture is to occlude temporarily one or more of the trackable markers on the tracked object (e.g. a probe) for a period of time, causing loss of the CAS system's ability to track the object. A temporary visual occlusion of a certain length (or within a certain range of time), coupled with the tracked object being in the same position before the occlusion and after the occlusion, would be interpreted as an input gesture. A visual or audible indicator that a gesture has been recognized could be used to provide feedback to the surgeon.

If desired, the user may perform a gesture to indicate acceptance of an input provided by the user. When tracking system 22 is a visual tracking system, the gesture comprises visual occlusion of a predetermined portion of trackable tool 20. It is desirable that the occlusion occur for a predetermined occlusion period in order to avoid inadvertent recognition of a gesture.

Yet another example of such an input method is the use of tracking system 22 in combination with one or more trackable input devices 30. Defined with respect to the trackable input device 30 are one or more control points, which can be two-dimensional or three-dimensional. These control points are visually indicated on the trackable input device so that a surgeon can see them. For example, the control points may be visually defined on an object by representations of buttons, numbers, letters, words, slides and/or other conventional input devices. The geometric relationship between each control point and trackable input device 30 is known and stored in processor-based system 16. Thus, the processor can determine when another trackable object touches or is in close proximity to a defined control point and recognize it as an indication of a user input to the processor-based systems. For example, when a tip of a tracked pointer is brought into close proximity to one of the defined control points, the processor-based system will recognize the tool near the defined control point and treat it as a user input associated with that defined control point. Preferably, representations on the trackable user input correspond to user input selections (e.g. buttons) on a graphical user interface 36 (FIG. 2A) on display device 12. The trackable input device may be formed on the surface of any type of trackable device, including devices used for other purposes. In a preferred embodiment, representations of user input functions for graphical user interface are visually defined on a rear, flat surface of a base of a tool calibrator. If desired, the trackable input device may be disposable.

Processor-based system 16 is, in one example, a programmable computer that is programmed to execute only when single-use or multiple-use software is loaded from, for example, removable media. The software would include, for example software application 34 for use with a specific type of procedure. Media storing the software application can be sold bundled with disposable instruments specifically intended for the procedure. The application program would be loaded into the processor-based system and stored there for use during one (or a defined number) of procedures before being disabled. Thus, the application program need not be distributed with the CAS system. Furthermore, application programs can be designed to work with specific tools and implants and distributed with those tools and implants. Preferably also the most current core CAS utilities may also be stored with the application program. If the core CAS utilities on the processor-based system are outdated, they can be replaced with the most current utilities.

The method described below utilizes preoperative CT data sets, i.e. CT scans made prior to surgery. Although CT scans offer certain advantages, if desired, image data sets obtained using other two-dimensional or three-dimensional imaging modalities, such as MRI, PET etc. may be used. Furthermore, the image data sets used may be those obtained pre-operatively or intra-operatively. If desired, the image data sets may be time variant, i.e. image data sets taken at different times may be used. Software application 34 may provide visual, auditory or tactile feedback to the user.

Figure 3:
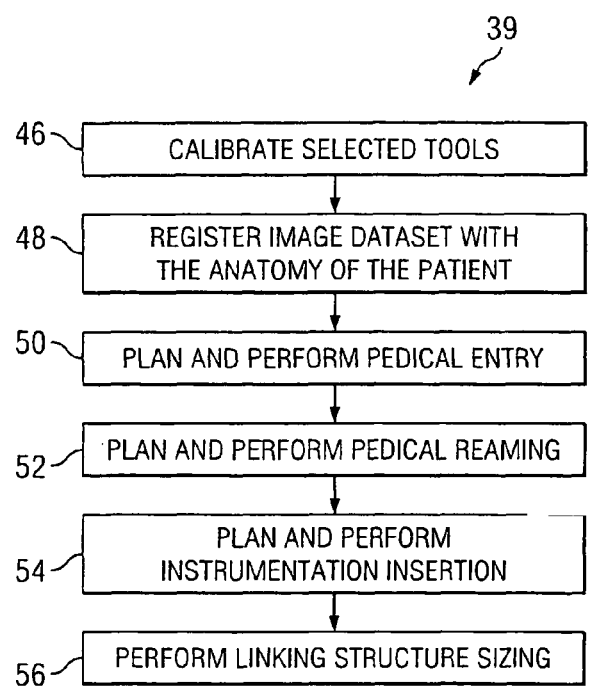
FIG. 3 is a flowchart of an exemplary method for performing a procedure.

FIGS. 2A-2F are exemplary screen displays 35, 37, 47, 49, 51, and 53 illustrating an exemplary user interface 36. FIG. 3 is a flowchart of an exemplary method 39 for performing a procedure. Method 39 is preferably used during a spinal fixation procedure. Method 39 is simply an exemplary method of a medical procedure in which method 60 (FIGS. 6A and 6B) described herein may be used. Method 60 may be used to assist in any medical procedure and is not limited to a spinal fixation procedure.

User interface 36 is used to guide the user through one or more steps of the medical procedure and to provide the user with visual and/or voice prompts during the process. Software application 34 also provides visual and/or voice feedback to the user via user interface 36. It should be noted that software application 34 does not require the user to perform each of the steps. Furthermore, it does not require the user to perform the steps in sequence. At any time during the procedure the user may cause software application 34 to move from one screen to another. Any method now known or later developed may be used for causing software application to move from one screen to another.

Figure 5:
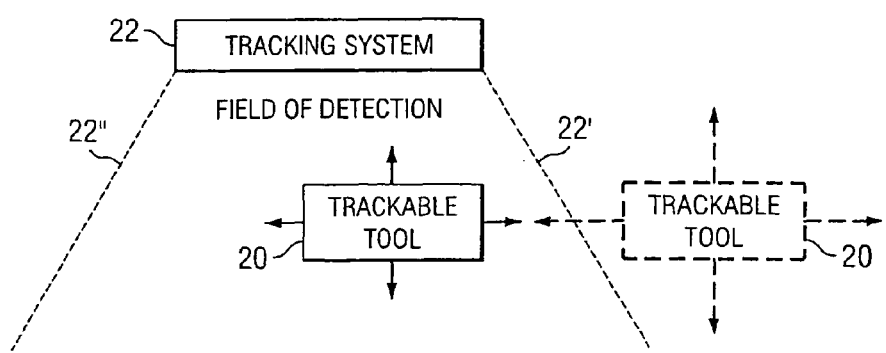
FIG. 5 is a schematic representation of a trackable tool detection functionality of the interactive computer-assisted surgery system.

For example, the user may select a "next screen" icon 31 or a "previous screen" icon 33 on display device 12 to move from one screen to another. The user may also proceed to a different step or screen by simply indicating the tool that the user is going to use next. The user may indicate the tool, for example, by simply picking the tool and bringing it into the field of detection of tracking system 22 (as shown in FIG. 5). Software application 34 determines which tool has been selected by the user and automatically displays the screen relevant to the selected tool. For example, if the user picks up a pedicle entry tool, then software application 34 automatically displays the pedicle entry screen 47 (FIG. 2C) on display device 12 so that step 50 of method 39 may be executed. The method of automatically displaying the relevant screen based on the selected tool is discussed in detail hereinafter with reference to the flowchart of FIGS. 6A and 6B.

Figure 4:
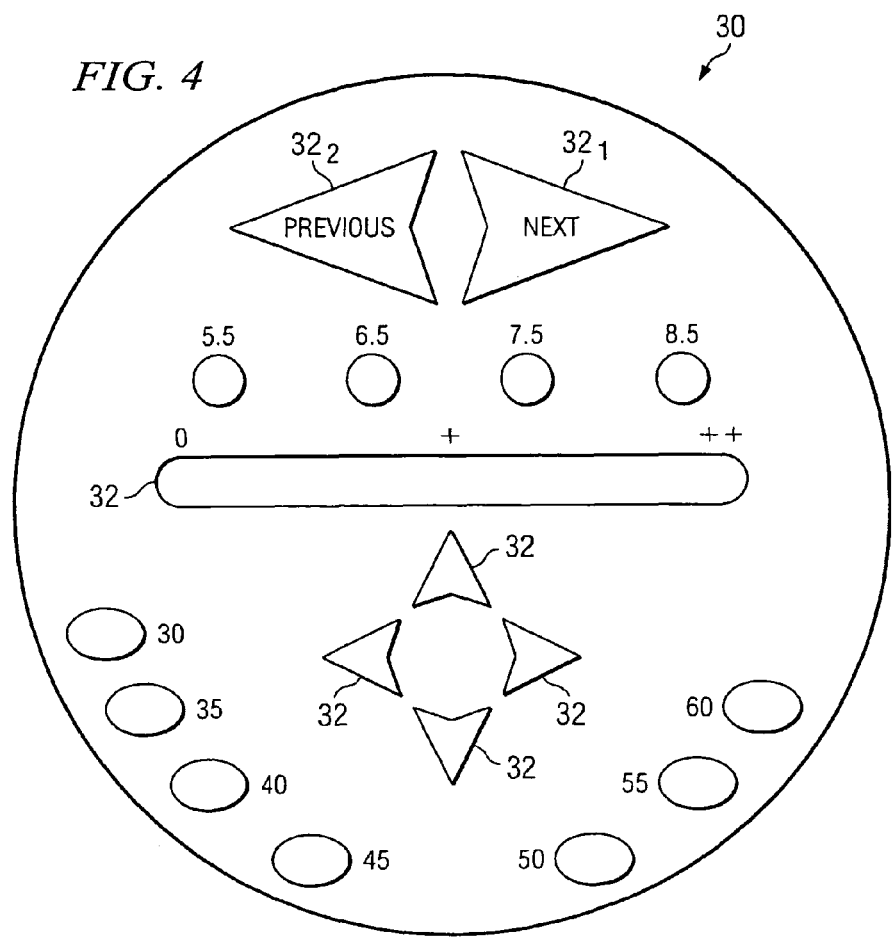
FIG. 4 is a schematic representation of a trackable input device.
Figure 6A:
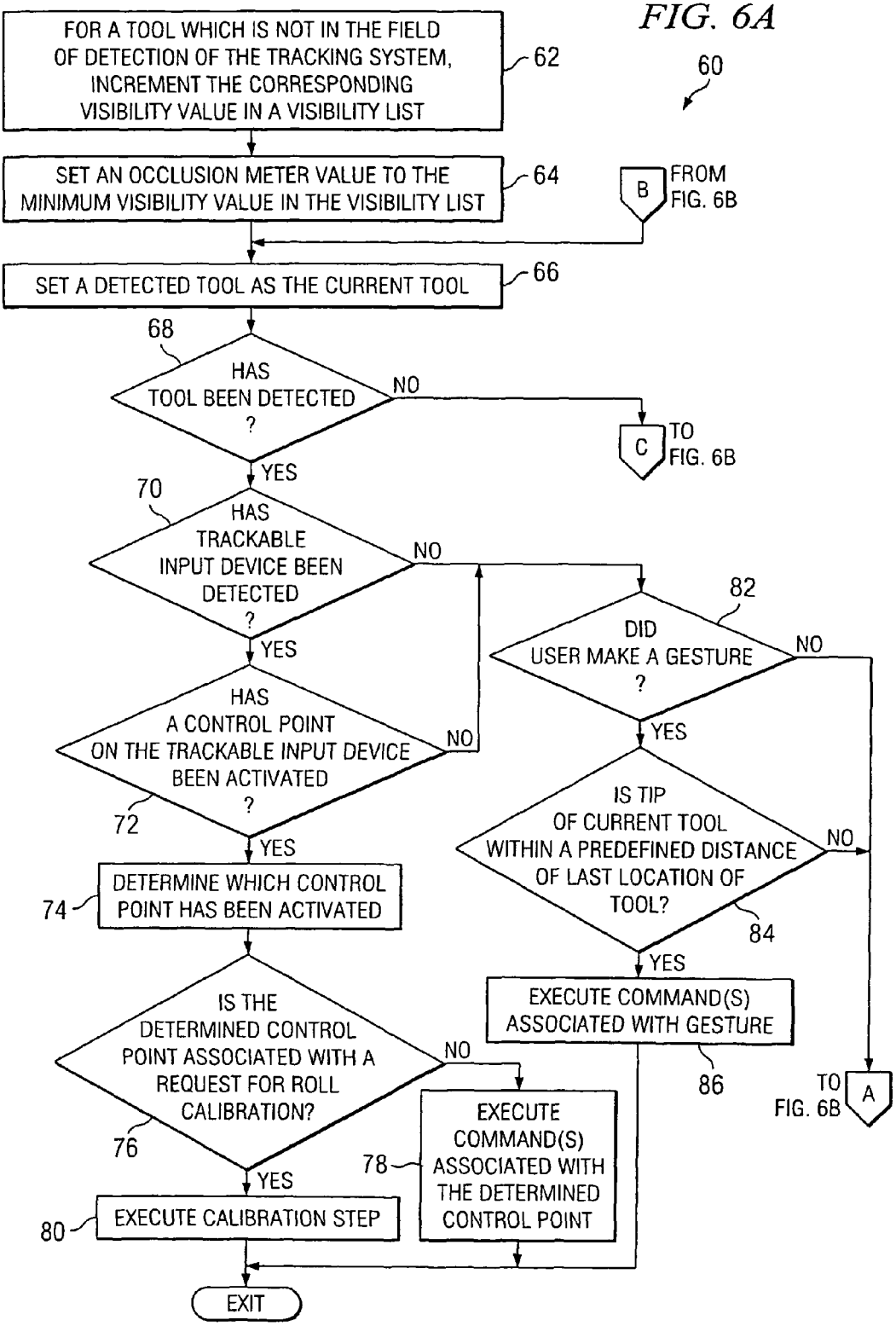
FIGS. 6A and 6B are flowcharts of an exemplary method for gesture control.
Figure 6B:
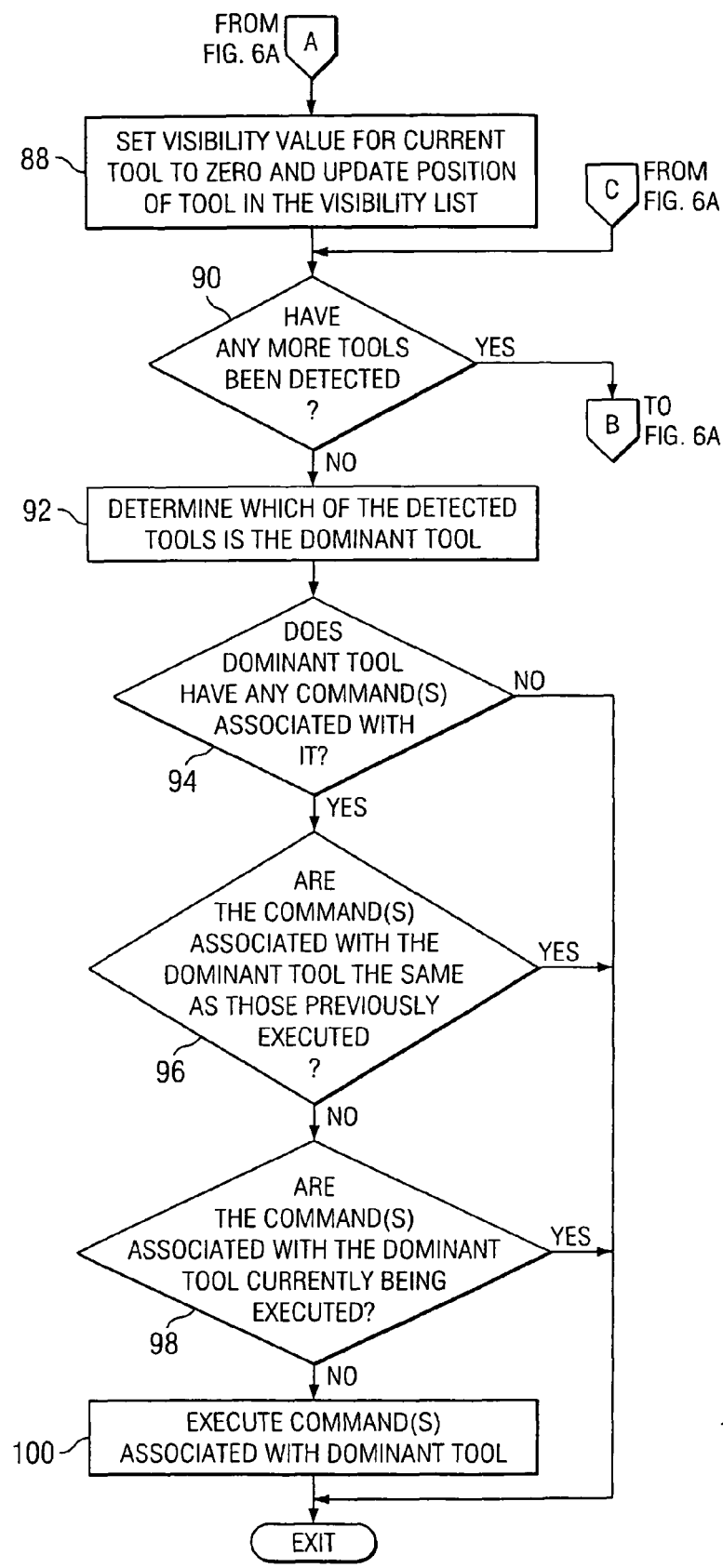

If desired, the user may navigate through the different steps by using trackable input device 30 as discussed in detail herein with reference to FIGS. 4, 6A and 6B.

Method 39 comprises of one or more of the following steps: calibration of tools selected for the procedure (step 46), registration of pre-operative image data sets with the anatomy of the patient (step 48), planning and performance of pedicle entry (step 50), planning and performance of pedicle reaming (step 52), planning and performance of instrumentation insertion (step 54) and performance of linking structure sizing (step 56). The steps for spinal fixation of method 39 are exemplary steps used in a spine linking procedure. Method 60 of FIGS. 6A and 6B is not limited to procedures that include the above steps but may be used to assist in any medical procedure.

Figure 2A:
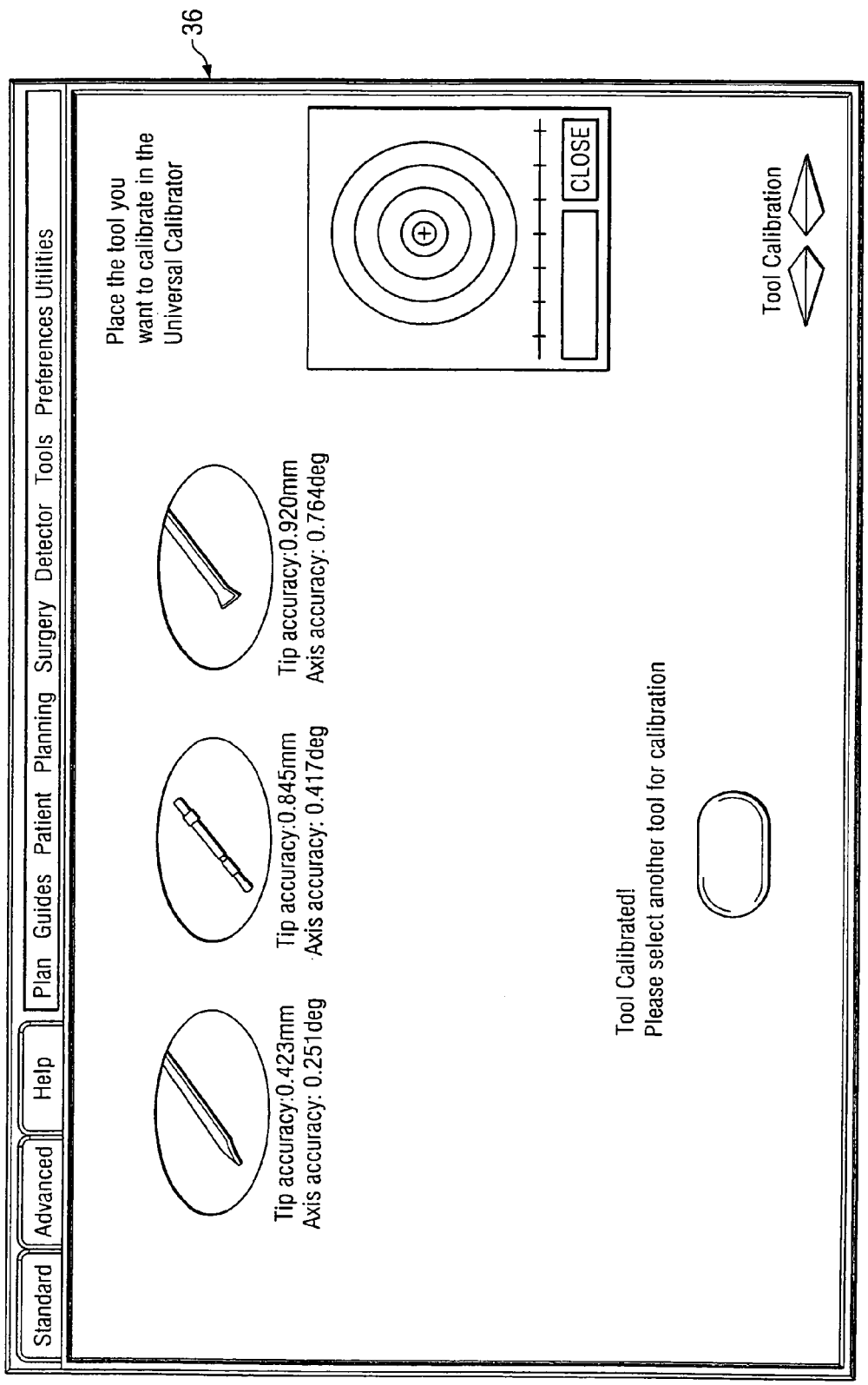
FIGS. 2A-2F are exemplary screen displays illustrating an exemplary graphical user interface of the interactive computer-assisted surgery system of FIG. 1.
Figure 2B:
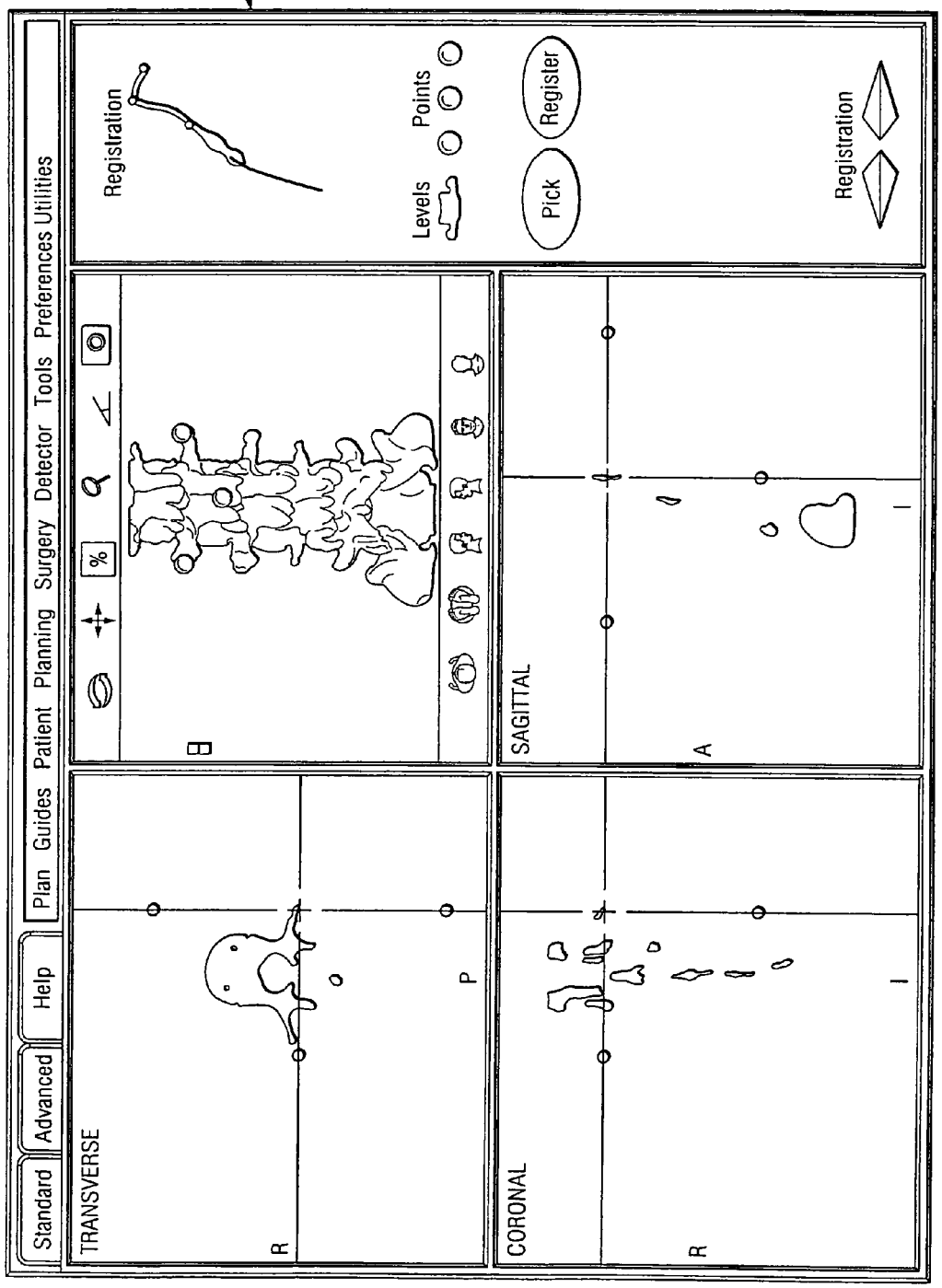
Figure 2C:
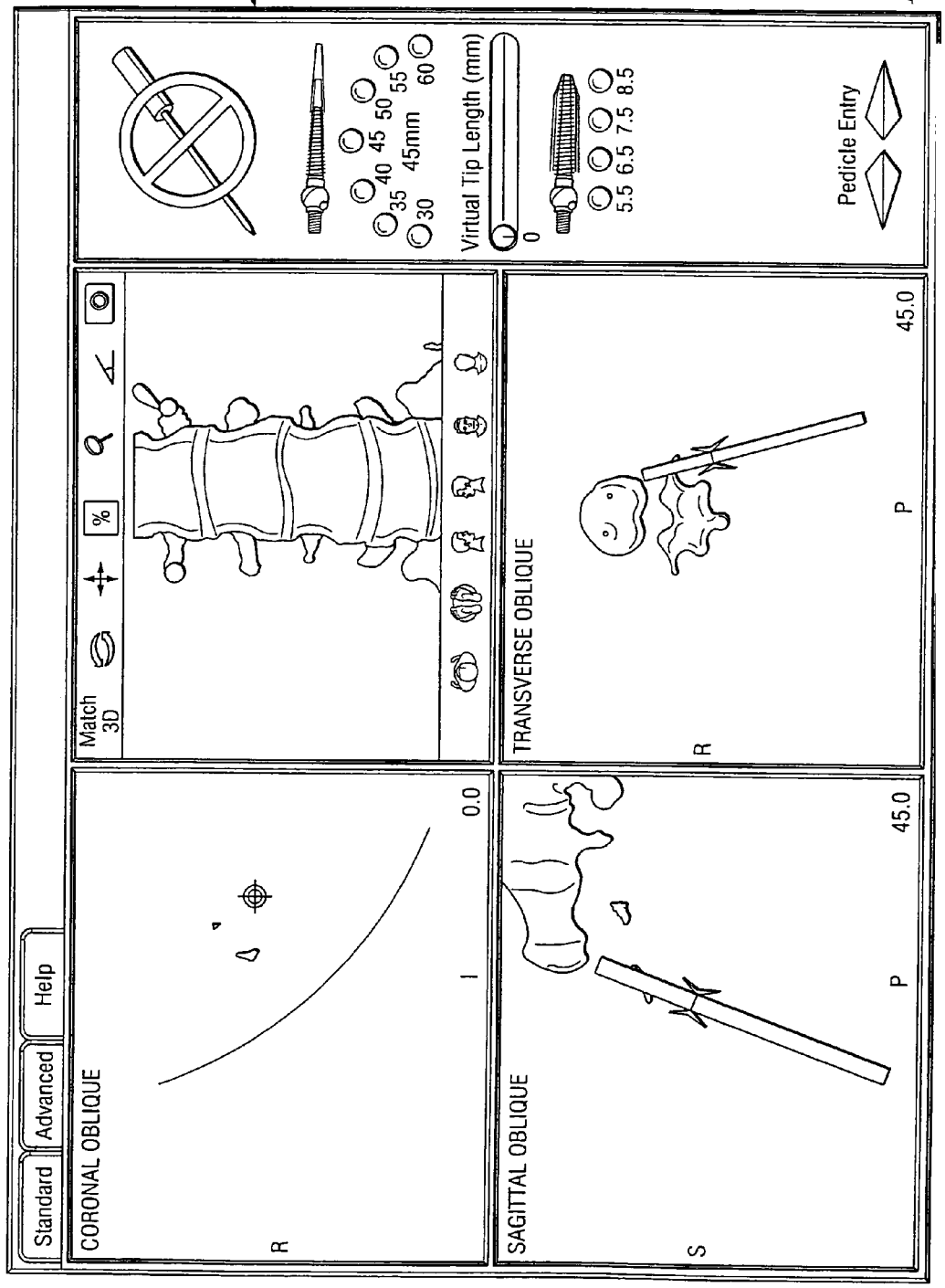

As shown in FIG. 2A, during step 46, user interface 36 displays images of tools previously selected by the user and prompts the user to calibrate a tool for use with the CAS system. The tools may be calibrated using any method for calibration now known or later developed, for example by placing the tool in a tool calibrator and moving it in a predetermined manner. The user may calibrate the tools in any order. Software application 34 automatically recognizes the tool and calibrates it. Once the tool has been calibrated, user interface 36 informs the user and prompts the user to calibrate another tool. This process is repeated until all tools to be used during the procedure have been calibrated.

User interface 36 then automatically displays a registration screen 37 (FIG. 2B) so that step 48 may be executed. In step 48, user interface 36 guides the user through the registration step, for example by prompting the user to indicate fiducials on the anatomy of the patient that correspond to fiducials previously selected by the user. In order to indicate a fiducial, the user places the tip of a trackable tool 20, for example a probe, on the portion of the anatomy of the patient corresponding to the fiducial previously selected by the user. The user may indicate that the portion pointed by the tip of trackable tool 20 is the selected fiducial by any mechanism now known or later developed. In a preferred embodiment, the user indicates the selection by a "gesture". Software application 34 recognizes the gesture and determines the position of the tip of the probe. The user may make a gesture with respect to trackable tool 20. The gesture is sensed or recognized by tracking system 22. The process of gesture recognition is discussed in further detail herein with reference to the flowchart of FIGS. 6A and 6B.

Once the user has identified fiducials on the anatomy of the patient, software application 34 calculates the registration error, if any, and informs the user of the error. If the error is not acceptable to the user, the user may choose to repeat the registration step, for example by selecting a "re-pick" icon, or any other method. If the registration error is acceptable to the user, the user may proceed to a different step of the procedure.

The pedicle entry screen 47 allows the user to plan an insertion point for an implant, for example a screw. It tracks and displays in real-time on display device 12 the position of the pedicle entry tool with respect to the image data set. A virtual tool tip may be displayed at the end of the image of the pedicle entry tool to further assist the user in planning an insertion point. If an implant is intended to be coupled to the tip of the tool, an image of the selected implant may be displayed coupled to the end of the tool to enable the user to track the actual position of the implant.

Software application 34 guides the user through steps 52 (FIG. 2D), 54 (FIG. 2E), and/or 56 (FIG. 2F) depending on the selections made by the user, for example by navigating using display device 12 or by simply selecting the tools for particular steps, for example pedicle reaming tool for step 52, an instrumentation insertion tool for step 54, and/or a probe for step 56.

FIG. 4 is a schematic diagram of trackable input device 30. Trackable input device 30 may be used to provide input to processor-based system 16. The input may be used to control the display on display device 12. Trackable input device 30 may be any trackable object, such as a trackable tool, device, and/or instrument. Trackable input device 30 preferably comprises a plurality of control points 32. One or more of the control points may be programmed or have instructions associated with it such that when the control point is activated, the instructions associated with the activated control point may be executed. For example, if control point $32_1$ is activated, then the display on display device 12 changes to the next screen and if control point $32_2$ is activated, then the display on display device 12 changes to the previous screen. The control points may be programmed and/or instructions associated with the control point in any manner now known or later developed. For example, a data file may contain a list of control points along with position information about the control points. The same data file or a different data file may include software scripts associated with the different control points. If desired, instructions associated with a particular control point may be included in a bar code which may be located in proximity to the control point. Alternatively, the bar code may have a pointer to a data file that contains the instructions to be executed upon activation of the control point.

The number of control points used, their shapes, and/or their positions on trackable input device 30 as illustrated in FIG. 4 are exemplary only. It is desirable, although not necessary, for ease of use that all the control points be provided on the same surface of trackable input device 30. The control points may be on a surface facing toward or away from tracking system 22.

If desired, one or more of control points 32 may be built into trackable input device 30, for example by engraving the control points onto the surface of trackable input device 30. In an alternative embodiment, one or more of control points 32 may be printed on a medium, for example a paper, and removably fixed to the surface of trackable input device 30. In such an embodiment, the same trackable input device may be used for different procedures, for example, spine fixation, knee replacement, hip replacement, etc.

An exemplary method for detecting which control point has been activated is discussed herein with reference to FIGS. 6A and 6B.

Figure 2D:
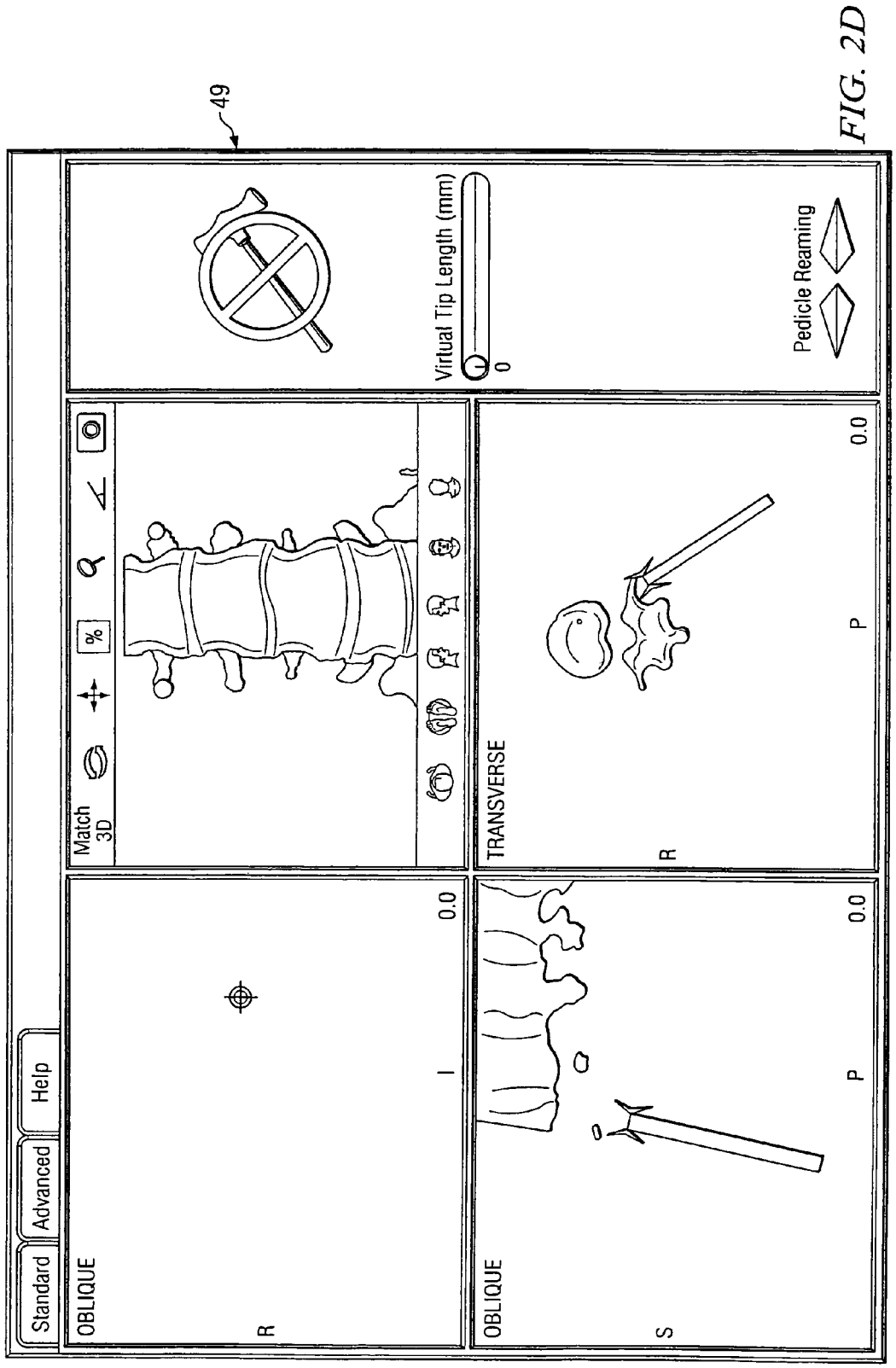
Figure 2E:
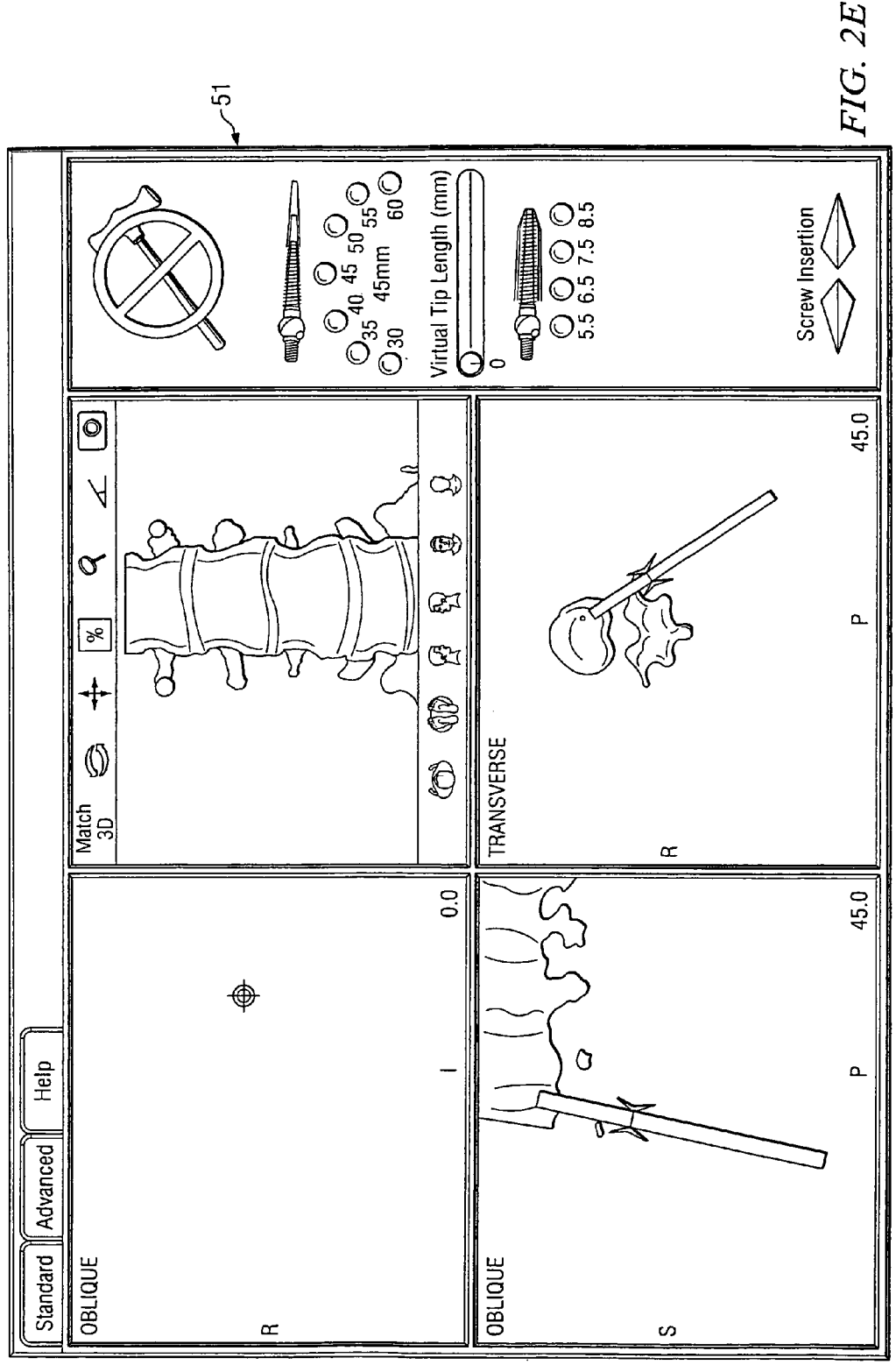
Figure 2F:
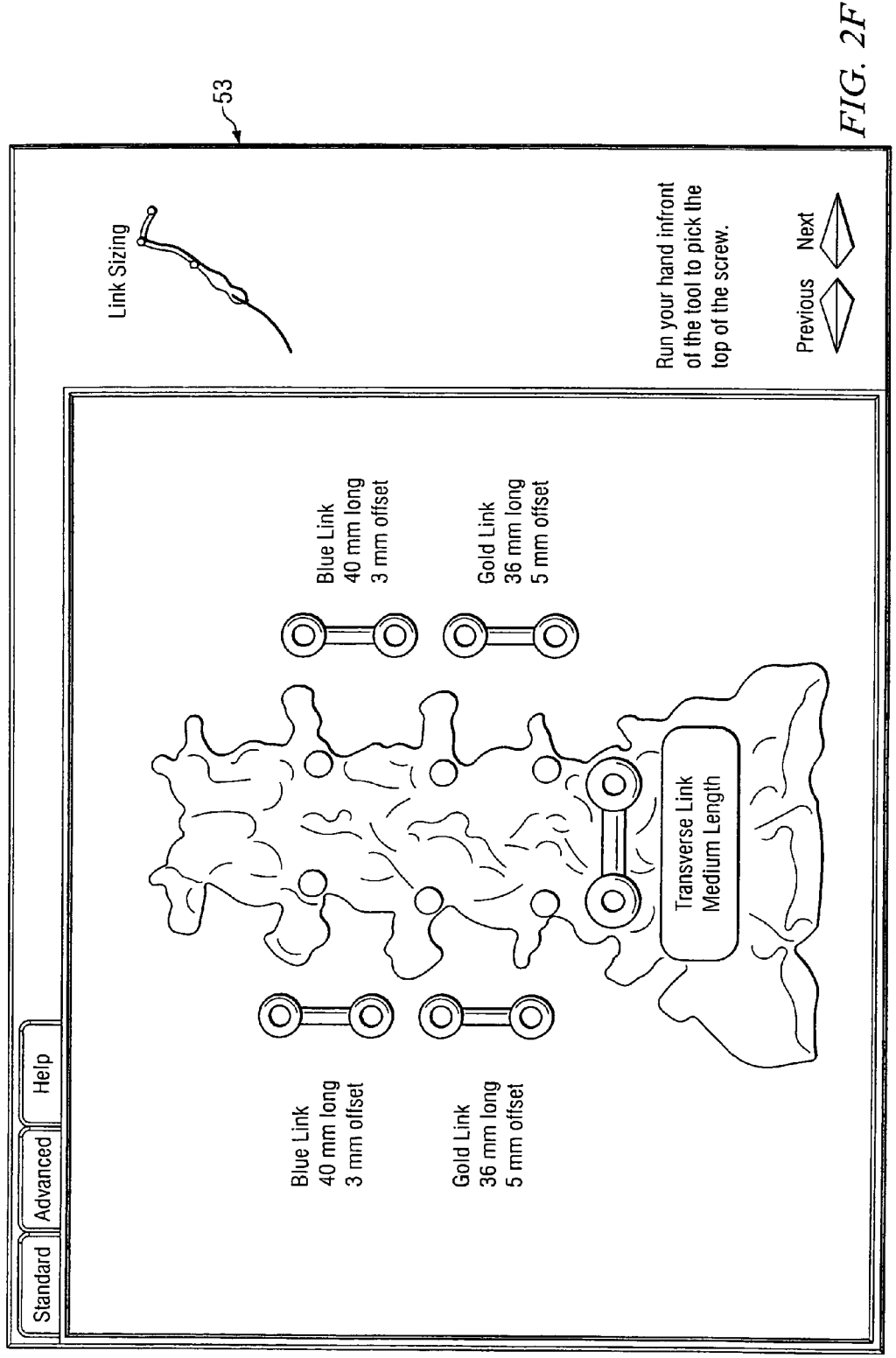

FIG. 5 is a schematic representation of a trackable tool detection functionality of software application 34. Tracking system 22 has a predetermined field of detection. An exemplary field of detection of tracking system 22 lies between dashed lines 22' and 22" of FIG. 5. In FIG. 5, trackable tool 20 is initially outside (as shown by dashed lines) the field of detection of tracking system 22. However, trackable tool 20 may be moved inside the field of detection of tracking system 22, for example when the user picks up trackable tool 20 for use. When trackable tool 20 is within the field of detection of tracking system 22, software application 34 automatically transitions to the relevant stage of the procedure and the screen on display device 12 may automatically be changed to the relevant screen. For example, if a pedicle reaming tool comes within the field of detection of tracking system 22, for example when the user picks up or otherwise indicates selection of the pedicle reaming tool, the screen on display device 12 is automatically changed to the pedicle reaming screen 49 (FIG. 2D).

FIGS. 6A and 6B are flowcharts of an exemplary method 60 for gesture control. In an exemplary embodiment, method 60 is executed periodically.

In an exemplary embodiment, a visibility list is maintained on processor-based system 16 and/or a removable medium. The visibility list comprises entries for a plurality of tools, for example tools that may be used during a procedure. Each tool has a tool ID associated with it. The tool ID may be based on one or more trackable elements associated with the tool. Preferably, the entry for a particular tool includes information, such as tool ID, tool position, a visibility value, and/or the like, for the tool. The visibility value for a tool corresponds to the number of iterations of method 60 that the particular tool was not detected or was not within the field of detection of tracking system 22.

In step 62, the visibility value for a tool which is not in the field of detection of tracking system 22 is incremented. In step 64, an occlusion meter value is set to the minimum visibility value in the visibility list. The occlusion meter value is used to keep track of the number of iterations for which a predetermined portion, for example a trackable element, of trackable tool 20 has been occluded.

In step 66, a tool in the field of detection of tracking system 22 is set as the current tool. In step 68, a determination is made as to whether the tool has been detected within the field of detection of tracking system 22. This step provides a redundant step to confirm that the current tool is within the field of detection of tracking system 22. If the current tool is not within the field of detection of tracking system 22, then the process starting at step 90 may be executed. Otherwise, in step 70, a determination is made as to whether trackable input device 30 has been detected within the field of detection of tracking system 22. In general, if trackable input device 30 is not within the field of detection of tracking system 22, then it is not likely that trackable input device 30 will be used to provide input to system 10. If it is determined that trackable input device 30 is not within the field of detection of tracking system 22, then the process starting at step 82 may be executed.

If trackable input device is not within the field of detection, then in step 72 a determination is made as to whether any of the control points 32 on trackable input device 30 has been activated. In an exemplary embodiment, each control point has a predefined distance associated with it. If desired, one or more of the controls points may have the same predefined distance associated with them. If a predefined portion of trackable tool 20, for example the tip of trackable tool 20, comes within the predefined distance of the control point, then that control point may be activated. If the tip of trackable tool 20 is within a predefined distance of more than one control point, then the control point closest to the tip of trackable tool 20 is activated. Thus, in step 72, a determination is made as whether the tip of trackable tool 20 is within a predefined distance of any of the control points. If it is determined that none of the controls points on trackable input device 30 have been activated, then the process starting at step 82 may be executed. Otherwise, in step 74, a determination is made as to which control point has been activated. In step 76, a determination is made as to whether the activated control point is associated with a request for roll calibration of trackable tool 20. This determination may be made, for example, by determining whether the coordinates of the activated control point correspond to the coordinates of the roll calibration control point on trackable input device 30. If the activated control point is associated with a request for roll calibration, then in step 80, a calibration step, for example step 46 of the flowchart of FIG. 3 may be executed. Otherwise, in step 78, the commands associated with the determined control point may be executed.

In step 82, a determination is made as to whether the user made a gesture. If in step 82, it is determined that the user had made a gesture, then the process starting at step 84 may be executed. Otherwise, the process starting at step 88 may be executed.

In an exemplary embodiment, when tracking system 22 is a visual tracking system, a gesture may be made by the user, for example by visually occluding a predetermined portion of trackable tool 20, for example by visually occluding one or more trackable elements of trackable tool 20. If desired, a gesture may be made by the user by providing a signal from trackable tool 20 as an input. A trigger mechanism may be provided on trackable tool 20 for providing the signal. If desired, a gesture may be provided by the user providing a voice command. In an exemplary embodiment, a determination as to whether there was a gesture is made by determining whether the visibility value for the current tool (or the occlusion meter value) is within a predefined range of values. A visibility value of the tool (or the occlusion meter value) within the predefined range indicates that the tool was not in the field of detection of tracking system 22 for the predefined range of iterations. This combined with the fact that the tool is in the field of detection of tracking system 22 indicates that the user had made a gesture relative to the current tool.

Preferably, in order for a gesture to be recognized as an intended gesture, it is desirable that the predetermined portion be occluded for a predetermined occlusion period. This prevents an inadvertent gesture from being recognized as the desired gesture. In an exemplary embodiment, an occlusion meter is displayed on display device 12. The occlusion meter is a dynamic bar that provides a visual indication to the user about when to stop occluding the trackable elements. In the exemplary embodiment, the occlusion meter is initially red. A portion of the occlusion meter turns green when the trackable element is first occluded. After the first occlusion, the user only has a limited time or limited number of iterations of method 60 for terminating the occlusion to indicate a gesture. The occlusion meter provides an indication of the number of iterations (or the amount of time) remaining for the user to terminate the occlusion.

In step 84, a determination is made as to whether the tip of the current tool is within a predefined distance of the last location of the tool. This determination may be made, for example by comparing the current location of the tip of the tool with the position of the tip of the tool when it was last detected as recorded in the visibility list. This step is desirable so that an accurate reading of the position of the tip of the tool may be obtained. If the tip of the current tool is not within a predefined distance of the last location of the tool, then the process starting at step 88 may be executed. Otherwise, the process starting at step 86 may be executed. In step 86, the command associated with the gesture may be executed. The commands executed in this step may also depend on the step of the medical procedure being executed. For example, during the registration step (step 48), the position of the fiducial being pointed to by the tip of the tool may be stored and the next fiducial to be pointed may be highlighted.

Step 88 is executed when it is determined that there was no gesture or the tip of the tool had moved farther than the threshold value. In step 88, the visibility value of the current tool is set to zero and the position of the current tool in the visibility list is updated to its current position.

In step 90, a determination is made as to whether any more tools have been detected in the field of detection of tracking system 22. If additional tools have been detected then the process starting at step 66 may be executed. Otherwise, the process starting at step 92 may be executed. In step 92, a determination is made as to which of the detected tools is the dominant tool. In an exemplary embodiment, the tool which is closest to a predefined center is designated as the dominant tool. The predefined center may be, for example, the center of the anatomy being operated on, a reference associated with the anatomy being operated on, etc.

Each tracked tool may have one or more commands associated with it so that when that tool is determined to be the dominant tool, the commands associated with that tool may be automatically executed. In step 94, a determination is made as to whether the dominant tool has any command(s) associated with it. If the dominant tool does not have any command(s) associated with it, then the process ends. Otherwise, in step 96, a determination is made as to whether the command(s) associated with the dominant tool are the same as those previously executed. If the command(s) associated with the dominant tool are the same as those previously executed, then the process end. Otherwise, in step 98 a determination is made as to whether the command(s) associated with the dominant tool are currently being executed. If the command(s) associated with the dominant tool are currently being executed, then the process ends. Otherwise, in step 100, the command(s) associated with the dominant tool may be executed. After execution of the command(s) associated with the dominant tool, the process terminates. For example, if the dominant tool is a pedicle reaming tool, then in step 100, the display on display device 12 automatically changes to the pedicle reaming screen (FIG. 2D) and step 52 of the flowchart of FIG. 3 may be executed. The user does not have to manually navigate to the appropriate screen, for example the pedicle reaming screen. The user simply selects the relevant tool, for example by picking-up the tool. CAS system 10 recognizes the tool and automatically determines the appropriate screen to be displayed and automatically displays the appropriate screen, for example the pedicle reaming screen.

The commands executed in response to the selection of the dominant tool may also depend on the screen currently being displayed on display device 12. For example, if the screen currently being displayed is the calibration screen (FIG. 2A), then upon recognizing that the pedicle reaming tool has been selected by the user, the icon relating to the pedicle reaming tool may be selected on the calibration screen to assist the user in calibrating the selected pedicle reaming tool. Furthermore, if there are more than one tools in the field of detection of tracking system 22, then the dominant tool is automatically recognized based, for example on it's proximity to the center, and the commands/instructions relevant to the dominant tool executed.

If a tool being used for a particular operation is no longer detectable by tracking system 22, say when it is moved out of the field of detection of tracking system 22 or is otherwise blocked from tracking system 22, then this may be visually indicated on display device 12. An exemplary illustration is provided in FIG. 2C when the pedicle entry tool is no longer detectable by tracking system 22.

A technical advantage of an exemplary embodiment of the present invention is that it automatically detects selection of a tool and automatically displays a relevant screen on display device 12.

Embodiments of the present invention may be implemented in software, hardware, application logic or a combination of software, hardware and application logic. The software, application logic and/or hardware may reside on processor-based system 16 or on a removable storage medium. If desired, part of the software, application logic and/or hardware may reside on processor-based system 16 and part of the software, application logic and/or hardware may reside on the removable storage medium.

If desired, the different steps discussed herein may be performed in any order and/or concurrently with each other. Furthermore, if desired, one or more of the above described steps may be optional or may be combined without departing from the scope of the present invention.

While the invention has been particularly shown and described by the foregoing detailed description, it will be understood by those skilled in the art that various other changes in form and detail may be made without departing from the spirit and scope of the invention.

What is claimed is:

1. An apparatus for a medical procedure comprising:
   a memory which stores a series of interface images which assist a user with the medical procedure;
   a display which displays a selected interface image;
   a processor programmed to:
     receive signals indicative of a location and an identity of a tool in a field of view of a tool tracking system,
     based at least in part on the identity of the tool in the field of view, determine a stage of the medical procedure,
     select one of said series of interface images in response to an occlusion from the tracking system of a predetermined portion of said tool by said user for a predetermined interval of time based on the determined stage of the medical procedure and the identity of the tool, and
     cause the display to display the selected interface image with a location of the occluded tool remaining stationary.

2. The apparatus of claim 1, wherein said processor is further programmed to control the display to display a dynamic bar indicating a time period remaining for completing a predefined task.

3. The apparatus of claim 1, wherein the tool is a hand-held tool instrumented to (1) be tracked by the tracking system and (2) have an identity of the tool determined by the tracking system.

4. The apparatus of claim 3, wherein said processor is further programmed to:
   determine whether said tracking system has detected an additional tool;
   determine which of said tool and said additional tool is closest to a predefined point; and
   designate one of the tool and said additional tool as a dominant tool; and
   cause the display of the location of the dominant tool.

5. The apparatus of claim 4, wherein said processor is further programmed to automatically execute a command associated with said dominant tool.

6. The apparatus of claim 3, wherein said processor is programmed to:
   cause the display to display the selected one of said series of interface images in response to a predetermined portion of said tool being out of the field of view of said tracking system during a predetermined period of time.

7. An apparatus for a medical procedure comprising:
   a memory which stores a series of interface images which assist a user with the medical procedure;

a display which displays a selected interface image;
a processor programmed to:
- receive signals indicative of an identity of a tool in a field of view of a tool tracking system,
- based at least in part on the identity of the tool in the field of view, determine a stage of the medical procedure,
- select one of the series of interface images based on the determined stage of the medical procedure and the identity of the tool,
- cause the display to display the selected interface image,
- receive signals indicative of a location of the tool in the field of view of the tool tracking system,
- determine whether the tool in the field of view of the tracking system is occluded,
- determine how long the tool remains occluded, and
- cause the display to display a visual indication of the occlusion, the visual indication of the occlusion including an occlusion meter.

8. The apparatus of claim 7, wherein said processor is further programmed to cause the display to change a color of at least a portion of said occlusion meter upon occlusion of a predetermined portion of said tool, a length of said portion indicating an elapsed time since initiation of said occlusion.

9. The apparatus of claim 8, wherein a length of a portion of said occlusion meter indicates how long the tool has been occluded from the tracking system.

10. The apparatus of claim 8, wherein said processor is further programmed to control the display to revert the color of said portion of said occlusion meter to a color indicative of no occlusion upon termination of said occlusion.

11. The apparatus of claim 7, wherein the tool is a hand-held tool instrumented to be optically tracked by the tracking system, the occlusion meter being indicative of a duration that the tool has been occluded from the tracking system by an intervening person or structure.

* * * * *